US008629888B1

(12) United States Patent
Chen et al.

(10) Patent No.: US 8,629,888 B1
(45) Date of Patent: Jan. 14, 2014

(54) METHOD AND APPARATUS FOR PERFORMING VIRTUAL PULLBACK OF AN INTRAVASCULAR IMAGING DEVICE

(71) Applicant: Volcano Corporation, San Diego, CA (US)

(72) Inventors: Sara Chen, Arcadia, CA (US); Edrienne Brandon, San Diego, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/764,149

(22) Filed: Feb. 11, 2013

Related U.S. Application Data

(63) Continuation of application No. 13/723,774, filed on Dec. 21, 2012.

(51) Int. Cl.
*G09G 5/00* (2006.01)

(52) U.S. Cl.
USPC .......................... 345/632; 345/619; 345/629

(58) Field of Classification Search
USPC .......... 345/619, 629–633; 600/407, 424–426; 715/754, 764, 856–861
See application file for complete search history.

(56) References Cited

U.S. PATENT DOCUMENTS

| | | | | |
|---|---|---|---|---|
| 5,202,961 | A * | 4/1993 | Mills et al. | 715/720 |
| 6,781,597 | B1 * | 8/2004 | Vrobel et al. | 345/619 |
| 7,930,014 | B2 | 4/2011 | Huennekens et al. | |
| 8,298,147 | B2 | 10/2012 | Huennekens et al. | |
| 2006/0241465 | A1 * | 10/2006 | Huennekens et al. | 600/458 |
| 2007/0038061 | A1 * | 2/2007 | Huennekens et al. | 600/407 |
| 2010/0094124 | A1 * | 4/2010 | Schoonenberg et al. | 600/424 |
| 2010/0290693 | A1 * | 11/2010 | Cohen et al. | 382/134 |
| 2012/0059253 | A1 * | 3/2012 | Wang et al. | 600/427 |
| 2012/0249531 | A1 * | 10/2012 | Jonsson | 345/419 |
| 2012/0265269 | A1 * | 10/2012 | Lui et al. | 607/46 |
| 2012/0320080 | A1 * | 12/2012 | Giese et al. | 345/619 |

FOREIGN PATENT DOCUMENTS

WO WO 2009106784 A1 * 9/2009

OTHER PUBLICATIONS

Johan H.C. Reiber, Shengxian Tu, Joan C. Tuinenburg, Gerhard Koning, Johannes P. Janssen, Jouke Dijkstra, QCA, IVUS and OCT in interventional cardiology in 2011, 2011, Cardiovascular Diagnosis and Therapy, 1(1):57-70 DOI: 10.3978/j.issn.2223-3652.2011.09.03.*

(Continued)

*Primary Examiner* — Aaron M Richer
*Assistant Examiner* — Michael J Cobb
(74) *Attorney, Agent, or Firm* — Haynes and Boone, LLP

(57) ABSTRACT

The present disclosure provides a method of displaying an intravascular procedure in a virtual environment. The method includes displaying information from a first view and a second view simultaneously. The first view contains virtual representations of an anatomical region of a human body and an intravascular imaging device disposed in the anatomical region. The second view contains a cross-sectional image of a segment of the anatomical region corresponding to a location of the intravascular imaging device. The method includes moving, in response to a user input, the virtual representation of the intravascular imaging device with respect to the virtual representation of the anatomical region. The method includes updating the cross-sectional image as the virtual representation of the intravascular imaging device is being moved. The updated cross-sectional image corresponds to a new location of the intravascular imaging device.

28 Claims, 7 Drawing Sheets

(56) References Cited

OTHER PUBLICATIONS

Voros et al., Prospective Validation of Standardized, 3-Dimensional, Quantitative Coronary Computed Tomographic Plaque Measurements Using Radiofrequency Backscatter Intravascular Ultrasound as Reference Standard in Intermediate Coronary Arterial Lesions, 2011, JACC: Cardiovascular Interventions, 4(2) 198-208.*

Gary S. Mintz, A Futuristic Vision of Next Generation IVUS Imaging Systems, 2006, Cardiovascular Research Foundation, www.summitmd.com (accessed Apr. 24, 2013).*

* cited by examiner

METHOD AND APPARATUS FOR PERFORMING VIRTUAL PULLBACK OF AN INTRAVASCULAR IMAGING DEVICE

PRIORITY DATA

This application is a Continuation Application of U.S. patent application Ser. No. 13/723,774, filed on Dec. 21, 2012, entitled "Method and Apparatus For Performing Virtual Pullback of an Intravascular Imaging Device," the entire disclosure of which is incorporated herein by reference in its entirety.

TECHNICAL FIELD

The present disclosure relates generally to intravascular imaging, and in particular, to a method and apparatus for performing a virtual pullback of an intravascular imaging device.

BACKGROUND

Intravascular imaging is widely used in interventional cardiology as a diagnostic tool for assessing a vessel, such as an artery, within the human body to determine the need for treatment, to guide intervention, and/or to assess its effectiveness. An imaging system such as an intravascular ultrasound (IVUS) system uses ultrasound echoes to form a cross-sectional image of the vessel of interest. Typically, IVUS imaging uses a transducer on an IVUS catheter that both emits ultrasound signals (waves) and receives the reflected ultrasound signals. The emitted ultrasound signals (often referred to as ultrasound pulses) pass easily through most tissues and blood, but they are partially reflected by discontinuities arising from tissue structures (such as the various layers of the vessel wall), red blood cells, and other features of interest. The IVUS imaging system, which is connected to the IVUS catheter by way of a patient interface module, processes the received ultrasound signals (often referred to as ultrasound echoes) to produce a cross-sectional image of the vessel where the IVUS catheter is located.

Traditionally, an IVUS run is performed when an IVUS catheter is pulled back from a blood vessel. While the IVUS catheter is being pulled back, the transducer on the IVUS catheter captures cross-sectional ultrasound images of the blood vessel at various locations of the blood vessel. These images are saved to an IVUS system and may be reviewed and analyzed by a physician later. However, the physician may not know where in the blood vessel a particular ultrasound image is taken. As such, even if the physician spots a problem on the ultrasound image, it may be difficult for him/her to perform an accurate diagnosis because the blood vessel location corresponding to the particular ultrasound image may be unavailable.

Therefore, while conventional methods and apparatuses for performing intravascular imaging are generally adequate for their intended purposes, they have not been entirely satisfactory in every aspect.

SUMMARY

One aspect of the present disclosure involves a method of simulating an intravascular procedure in a virtual environment. The method includes: displaying information from a first view and a second view simultaneously, wherein the first view contains virtual representations of an anatomical region of a human body and an intravascular imaging device disposed in the anatomical region, and wherein the second view contains a cross-sectional image of a segment of the anatomical region corresponding to a location of the intravascular imaging device; moving, in response to a user input, the virtual representation of the intravascular imaging device with respect to the virtual representation of the anatomical region; and updating the cross-sectional image as the virtual representation of the intravascular imaging device is being moved, wherein the updated cross-sectional image corresponds to a new location of the intravascular imaging device.

Another aspect of the present disclosure involves an electronic apparatus configured to perform a virtual pullback of an intravascular imaging device. The electronic apparatus includes: a screen configured to display an output to the user; a memory storage component configured to store programming code; and a computer processor configured to execute the programming code to perform the following tasks: displaying, on the screen, information from a first view and a second view simultaneously, wherein the first view contains virtual representations of an anatomical region of a human body and an intravascular imaging device disposed in the anatomical region, and wherein the second view contains a cross-sectional image of a segment of the anatomical region corresponding to a location of the intravascular imaging device; moving, in response to a user input, the virtual representation of the intravascular imaging device with respect to the virtual representation of the anatomical region; and updating the cross-sectional image as the virtual representation of the intravascular imaging device is being moved, wherein the updated cross-sectional image corresponds to a new location of the intravascular imaging device.

Yet another aspect of the present disclosure involves an apparatus that includes a non-transitory, tangible machine-readable storage medium storing a computer program. The computer program contains machine-readable instructions that when executed electronically by computer processors, perform: displaying, on a touch-sensitive screen, information from a first view and a second view simultaneously, wherein the first view contains virtual representations of an anatomical region of a human body and an intravascular imaging device disposed in the anatomical region, and wherein the second view contains a cross-sectional image of a segment of the anatomical region corresponding to a location of the intravascular imaging device; moving, in response to a user input, the virtual representation of the intravascular imaging device with respect to the virtual representation of the anatomical region; and updating the cross-sectional image as the virtual representation of the intravascular imaging device is being moved, wherein the updated cross-sectional image corresponds to a new location of the intravascular imaging device.

Both the foregoing general description and the following detailed description are exemplary and explanatory in nature and are intended to provide an understanding of the present disclosure without limiting the scope of the present disclosure. In that regard, additional aspects, features, and advantages of the present disclosure will become apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
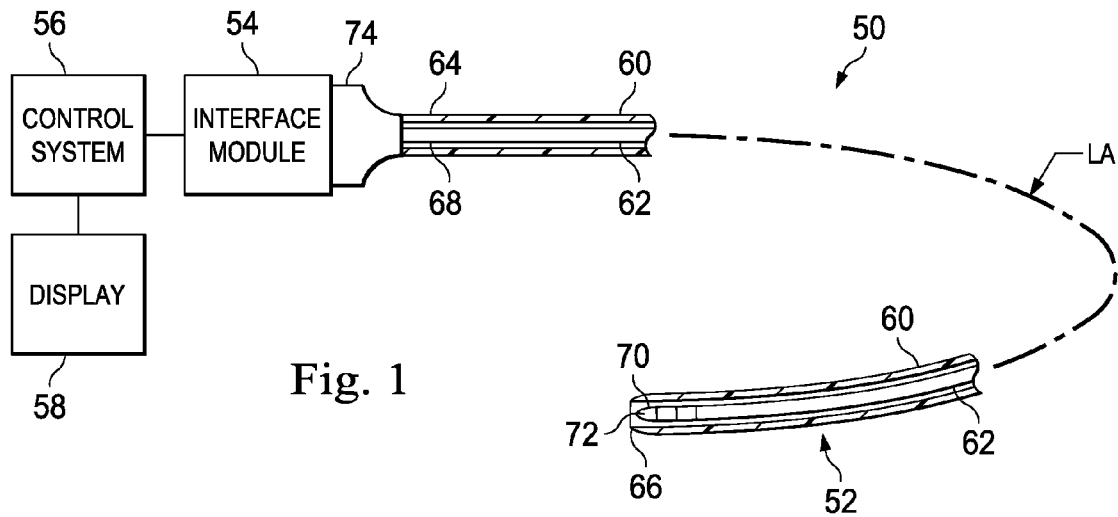
FIG. 1 is a schematic illustration of an intravascular ultrasound (IVUS) imaging system according to various aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, the present disclosure provides an ultrasound imaging system described in terms of cardiovascular imaging, however, it is understood that such description is not intended to be limited to this application, and that such imaging system can be utilized for imaging throughout the body. In some embodiments, the illustrated ultrasound imaging system is a side looking intravascular imaging system, although transducers formed according to the present disclosure can be mounted in other orientations including forward looking. The imaging system is equally well suited to any application requiring imaging within a small cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

There are primarily two types of catheters in common use today: solid-state and rotational. An exemplary solid-state catheter uses an array of transducers (typically 64) distributed around a circumference of the catheter and connected to an electronic multiplexer circuit. The multiplexer circuit selects transducers from the array for transmitting ultrasound signals and receiving reflected ultrasound signals. By stepping through a sequence of transmit-receive transducer pairs, the solid-state catheter can synthesize the effect of a mechanically scanned transducer element, but without moving parts. Since there is no rotating mechanical element, the transducer array can be placed in direct contact with blood and vessel tissue with minimal risk of vessel trauma, and the solid-state scanner can be wired directly to the imaging system with a simple electrical cable and a standard detachable electrical connector.

An exemplary rotational catheter includes a single transducer located at a tip of a flexible driveshaft that spins inside a sheath inserted into the vessel of interest. The transducer is typically oriented such that the ultrasound signals propagate generally perpendicular to an axis of the catheter. In the typical rotational catheter, a fluid-filled (e.g., saline-filled) sheath protects the vessel tissue from the spinning transducer and driveshaft while permitting ultrasound signals to freely propagate from the transducer into the tissue and back. As the driveshaft rotates (for example, at 30 revolutions per second), the transducer is periodically excited with a high voltage pulse to emit a short burst of ultrasound. The ultrasound signals are emitted from the transducer, through the fluid-filled sheath and sheath wall, in a direction generally perpendicular to an axis of rotation of the driveshaft. The same transducer then listens for returning ultrasound signals reflected from various tissue structures, and the imaging system assembles a two dimensional image of the vessel cross-section from a sequence of several hundred of these ultrasound pulse/echo acquisition sequences occurring during a single revolution of the transducer.

FIG. 1 is a schematic illustration of an ultrasound imaging system 50 according to various aspects of the present disclosure. In some embodiments, the ultrasound imaging system 50 includes an intravascular ultrasound imaging system (IVUS). The IVUS imaging system 50 includes an IVUS catheter 52 coupled by a patient interface module (PIM) 54 to an IVUS control system 56. The control system 56 is coupled to a monitor 58 that displays an IVUS image (such as an image generated by the IVUS system 50).

In some embodiments, the IVUS catheter 52 is a rotational IVUS catheter, which may be similar to a Revolution® Rotational IVUS Imaging Catheter available from Volcano Corporation and/or rotational IVUS catheters disclosed in U.S. Pat. No. 5,243,988 and U.S. Pat. No. 5,546,948, both of which are incorporated herein by reference in their entirety. The catheter 52 includes an elongated, flexible catheter sheath 60 (having a proximal end portion 64 and a distal end portion 66) shaped and configured for insertion into a lumen of a blood vessel (not shown). A longitudinal axis LA of the catheter 52 extends between the proximal end portion 64 and the distal end portion 66. The catheter 52 is flexible such that it can adapt to the curvature of the blood vessel during use. In that regard, the curved configuration illustrated in FIG. 1 is for exemplary purposes and in no way limits the manner in which the catheter 52 may curve in other embodiments. Generally, the catheter 52 may be configured to take on any desired straight or arcuate profile when in use.

A rotating imaging core 62 extends within the sheath 60. The imaging core 62 has a proximal end portion 68 disposed within the proximal end portion 64 of the sheath 60 and a distal end portion 70 disposed within the distal end portion 66 of the sheath 60. The distal end portion 66 of the sheath 60 and the distal end portion 70 of the imaging core 62 are inserted into the vessel of interest during operation of the IVUS imaging system 50. The usable length of the catheter 52 (for example, the portion that can be inserted into a patient, specifically the vessel of interest) can be any suitable length and can be varied depending upon the application. The proximal end portion 64 of the sheath 60 and the proximal end portion 68 of the imaging core 62 are connected to the interface module 54. The proximal end portions 64, 68 are fitted with a catheter hub 74 that is removably connected to the interface module 54. The catheter hub 74 facilitates and supports a rotational interface that provides electrical and mechanical coupling between the catheter 52 and the interface module 54.

The distal end portion 70 of the imaging core 62 includes a transducer assembly 72. The transducer assembly 72 is configured to be rotated (either by use of a motor or other rotary device or manually by hand) to obtain images of the vessel. The transducer assembly 72 can be of any suitable type for visualizing a vessel and, in particular, a stenosis in a vessel. In the depicted embodiment, the transducer assembly 72 includes a piezoelectric micromachined ultrasonic transducer ("PMUT") transducer and associated circuitry, such as an application-specific integrated circuit (ASIC). An exemplary PMUT used in IVUS catheters may include a polymer piezoelectric membrane, such as that disclosed in U.S. Pat. No. 6,641,540, hereby incorporated by reference in its entirety. The PMUT transducer can provide greater than 50% bandwidth for optimum resolution in a radial direction, and a spherically-focused aperture for optimum azimuthal and elevation resolution.

The transducer assembly 72 may also include a housing having the PMUT transducer and associated circuitry disposed therein, where the housing has an opening that ultrasound signals generated by the PMUT transducer travel through. In yet another alternative embodiment, the transducer assembly 72 includes an ultrasound transducer array (for example, arrays having 16, 32, 64, or 128 elements are utilized in some embodiments).

The rotation of the imaging core 62 within the sheath 60 is controlled by the interface module 54, which provides user interface controls that can be manipulated by a user. The interface module 54 can receive, analyze, and/or display information received through the imaging core 62. It will be appreciated that any suitable functionality, controls, information processing and analysis, and display can be incorporated into the interface module 54. In an example, the interface module 54 receives data corresponding to ultrasound signals (echoes) detected by the imaging core 62 and forwards the received echo data to the control system 56. In an example, the interface module 54 performs preliminary processing of the echo data prior to transmitting the echo data to the control system 56. The interface module 54 may perform amplification, filtering, and/or aggregating of the echo data. The interface module 54 can also supply high- and low-voltage DC power to support operation of the catheter 52 including the circuitry within the transducer assembly 72.

In some embodiments, wires associated with the IVUS imaging system 50 extend from the control system 56 to the interface module 54 such that signals from the control system 56 can be communicated to the interface module 54 and/or vice versa. In some embodiments, the control system 56 communicates wirelessly with the interface module 54. Similarly, it is understood that, in some embodiments, wires associated with the IVUS imaging system 50 extend from the control system 56 to the monitor 58 such that signals from the control system 56 can be communicated to the monitor 58 and/or vice versa. In some embodiments, the control system 56 communicates wirelessly with the monitor 58.

Figure 2:
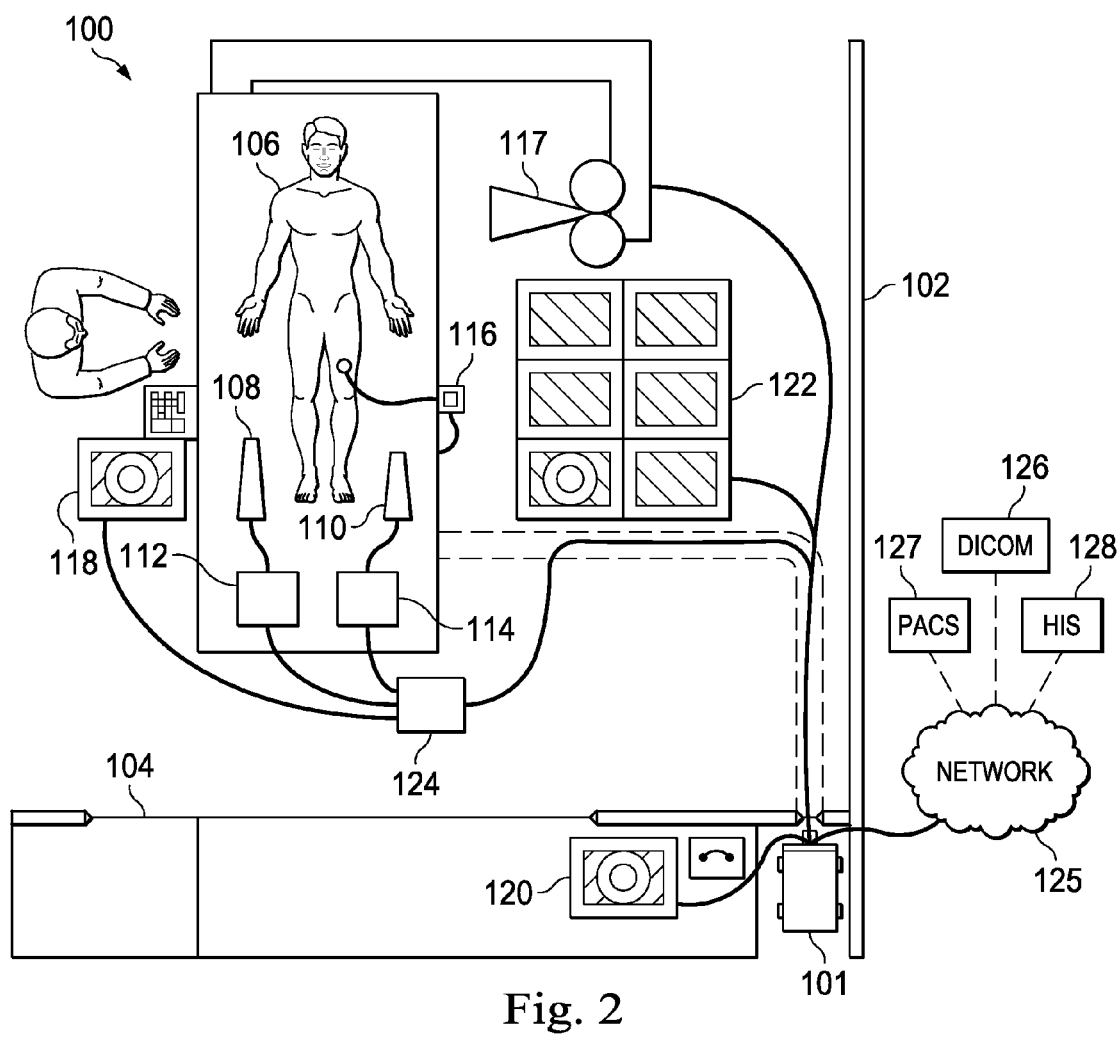
FIG. 2 is a schematic drawing depicting a medical sensing system including a multi-modality processing system according to one embodiment of the present disclosure.

FIG. 2 is a schematic drawing depicting a medical sensing system 100 including a multi-modality processing system 101 according to one embodiment of the present disclosure. In general, the medical sensing system 100 provides for coherent integration and consolidation of multiple forms of acquisition and processing elements designed to be sensitive to a variety of methods used to acquire and interpret human biological physiology and morphological information. More specifically, in system 100, the multi-modality processing system 101 is an integrated device for the acquisition, control, interpretation, and display of multi-modality medical sensing data. In one embodiment, the processing system 101 is a computer workstation with the hardware and software to acquire, process, and display multi-modality medical sensing data, but in other embodiments, the processing system 101 may be any other type of computing system operable to process medical sensing data. In the embodiments in which processing system 101 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller.

In the illustrated embodiment, the medical sensing system 100 is deployed in a catheter lab 102 having a control room 104, with the processing system 101 being located in the control room. In other embodiments, the processing system 101 may be located elsewhere, such as in the catheter lab 102 itself as will be described in association with FIGS. 3 and 4. The catheter lab 102 includes a sterile field but its associated control room 104 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. For example, in catheter lab 102 a patient 106 may be undergoing a multi-modality procedure either as a single procedure or in combination with one or more sensing procedures, in which IVUS data will be collected with an IVUS catheter 108 (which may be implemented as an embodiment of the IVUS catheter 52 of FIG. 1), and OCT data will be collected with an OCT catheter 110. In some embodiments, the IVUS catheter 108 may also include one or more sensors such as a phased-array transducer and may be capable of multi-modality sensing such as IVUS and IVPA sensing. The OCT catheter 110 may include one or more optical sensors.

In the embodiment illustrated in FIG. 2, the medical sensing system 100 includes a number of interconnected medical sensing-related tools in the catheter lab 102 and control room 104 to facilitate this multi-modality workflow procedure, including an IVUS patient isolation module (PIM) 112, an OCT PIM 114, an electrocardiogram (ECG) device 116, an angiogram system 117, a bedside control surface 118, a control room control surface 120, and a boom display 122. A bedside utility box (BUB) 124 in the catheter lab 102 acts as a hub for the PIMs 112 and 114, ECG device 116, and bedside control surface 118 and communicatively couples them to the processing system 101. In the illustrated embodiment, the angiography system 117, control room control surface 120, and boom display 122 are communicatively coupled directly to the processing system 101. However, in alternative embodiments, these tools may be coupled to the processing system 101 via the BUB 124. In one embodiment, the BUB 124 is a passive cable pass-through device that consolidates wires and feeds them into an under-floor cabling trench, but, alternatively, in other embodiments, the BUB 124 may contain logic and communication circuitry to actively coordinate communication between the medical sensing tools and the processing system 101. U.S. Provisional Patent Application No. 61/473,625, entitled "MEDICAL SENSING COMMUNICATION SYSTEM AND METHOD" and filed on Apr. 8, 2011, discloses a bedside utility box that intelligently couples medical sensing-related tools and is hereby incorporated by reference in its entirety. Further, the multi-modality processing system 101 is communicatively coupled to a data network 125. In the illustrated embodiment, the data network 125 is a TCP/IP-based local area network (LAN), however in other embodiments, it may utilize a different protocol such as Synchronous Optical Networking (SONET), or may be a wide area network (WAN). The processing system 101 may connect to various resources via the network 125. For example, the processing system 101 may communicate with a Digital Imaging and Communications in Medicine (DICOM) system 126, a Picture Archiving and Communication System (PACS) 127, and a Hospital Information System 128 through the network 125.

Additionally, in the illustrated embodiment, medical sensing tools in system 100 are communicatively coupled to the processing system 101 via a wired connection such as a standard copper link or a fiber optic link, but, in alternative embodiments, the tools may be connected to the processing system 101 via wireless connections using IEEE 802.11 Wi-Fi standards, Ultra Wide-Band (UWB) standards, wireless FireWire, wireless USB, or another high-speed wireless networking standard.

In the medical sensing system 100, the IVUS PIM 112 and OCT PIM 114 are operable to respectively receive medical sensing data collected from the patient 106 by the IVUS catheter 108 and OCT catheter 110 and are operable to transmit the received data to the processing system 101 in the control room 104. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. In one embodiment, the PIMs 112 and 114 include analog to digital (A/D) converters and transmit digital data to the processing system 101, however, in other embodiments, the PIMs transmit analog data to the processing system. Additionally, the ECG device 116 is operable to transmit electrocardiogram signals or other hemodynamic data from patient 106 to the processing system 101. In some embodiments, the processing system 101 may be operable to synchronize data collection with the catheters 108 and 110 using ECG signals from the ECG 116. Further, the angiogram system 117 is operable to collect x-ray, computed tomography (CT), or magnetic resonance images (MRI) of the patient 106 and transmit them to the processing system 101. In one embodiment, the angiogram system 117 may be communicatively coupled to the processing system 101 through the network 125, but, in other embodiments, the angiogram system may be more directly coupled to the processing system 101, for example through an adapter device. Such an adaptor device may transform data from a proprietary third-party format into a format usable by the processing system 101. In some embodiments, the processing system 101 may co-register image data from angiogram system 117 (e.g. x-ray data, MRI data, CT data, etc.) with sensing data from the IVUS and OCT catheters 108 and 110. As one aspect of this, the co-registration may be performed to generate three-dimensional images with the sensing data.

The bedside control surface 118 is also communicatively coupled to the processing system 101 via the BUB 124 and provides user control of the particular medical sensing modality (or modalities) being used to diagnose the patient 106. In the current embodiment, the bedside control surface 118 is a touch screen that provides user controls and diagnostic images on a single surface. In alternative embodiments, however, the bedside control surface 118 may include both a non-interactive display and separate controls such as physical buttons and/or a joystick. In the integrated medical sensing system 100, the bedside control surface 118 is operable to present workflow control options and patient image data in graphical user interfaces (GUIs). The bedside control surface 118 is capable of displaying GUIs for multiple modalities, and thus a clinician does not have to physically move between user interface devices when switching sensing modalities.

The control room control surface 120 in the control room 104 is also communicatively coupled to the processing system 101 and, as shown in FIG. 2, is adjacent to catheter lab 102. In the current embodiment, the control room control surface 120 is similar to the bedside control surface 118 in that it includes a touch screen and is operable to display multitude of GUI-based workflows corresponding to different medical sensing modalities. In some embodiments, the control room control surface 120 may be used to simultaneously carry out a different aspect of a procedure's workflow than the bedside control surface 118. In alternative embodiments, the control room control surface 120 may include a non-interactive display and standalone controls such as a mouse and keyboard.

The system 100 further includes the boom display 122 communicatively coupled to the processing system 101. The boom display 122 may include an array of monitors, each capable of displaying different information associated with a medical sensing procedure. For example, during an IVUS procedure, one monitor in the boom display 122 may display a tomographic view and one monitor may display a sagittal view.

Figure 3:
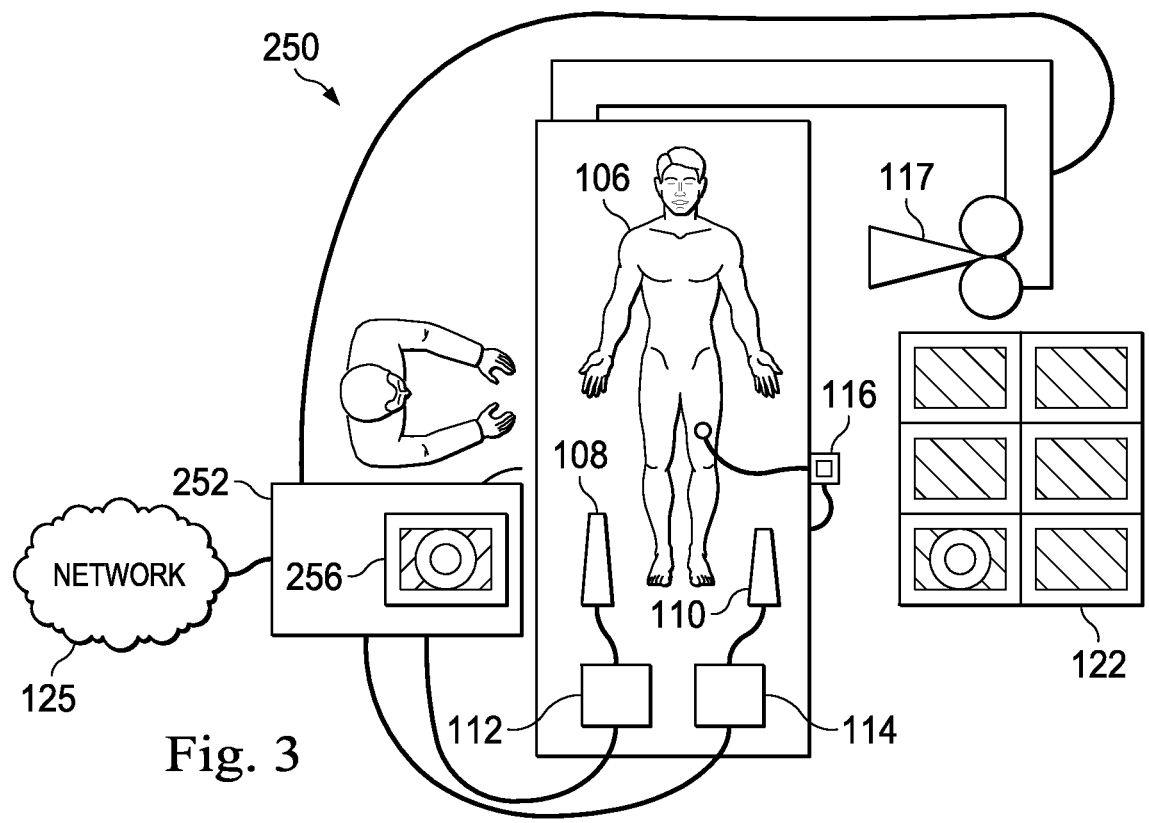
FIG. 3 is a schematic drawing depicting a medical sensing system including a multi-modality processing system according to another embodiment of the present disclosure.
Figure 4:
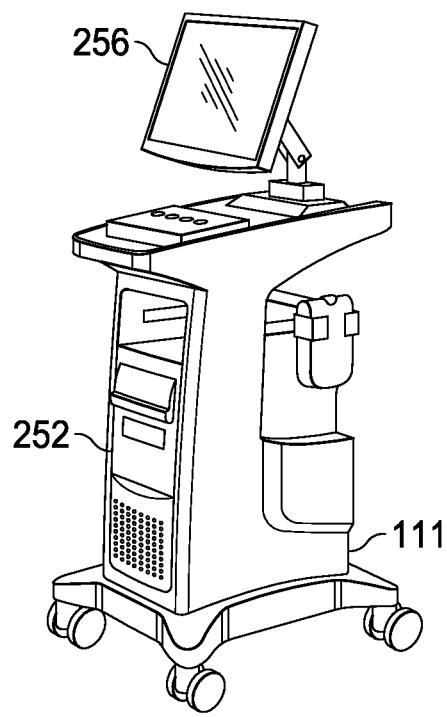
FIG. 4 is a diagrammatic perspective view of an aspect of the medical sensing system of FIG. 3, namely, the multi-modality processing system.

FIG. 3 is a schematic drawing depicting a medical sensing system 250 including a multi-modality processing system 252 according to another embodiment of the present disclosure. FIG. 4 is a diagrammatic perspective view of the multi-modality processing system 252 of FIG. 3. Like the processing system 101 in system 100, the multi-modality processing system 252 in medical sensing system 250 is an integrated device for the acquisition, control, interpretation, and display of multi-modality medical sensing data. In this regard, the processing system 250 contains a similar software framework as processing system 101.

However, the processing system 252 is mobile and may be moved between catheter labs. In the illustrated embodiment, the processing system 250 is currently located in catheter lab 102 to perform an IVUS and OCT workflow on patient 106. In the medical sensing system 250, the IVUS PIM 112, OCT PIM 114, ECG system 116, angiography system 117, boom display 122, and data network 125 are communicatively coupled to the processing system 250. Although the medical sensing tools in system 250 are shown as communicatively coupled to each other and the processing system 252 via a wired connection (e.g. standard copper link, a fiber optic link), the tools may be connected to the processing system 252 via wireless connections (e.g. IEEE 802.11 Wi-Fi, UWB, wireless FireWire, wireless USB) in other embodiments.

Further, as shown in FIG. 4, the processing system 252 sits on a wheeled cart 111 to facilitate the mobility of the system. In some embodiments, the cart 111 may include wire management systems to control the various wires attached to the system 252. Additionally, a controller 256 sits on the cart 111 and is communicatively coupled to the processing system 252. The controller 256 is operable to present a GUI to a clinician conducting a workflow. In the illustrated embodiment, the controller 256 is a touch screen that provides user controls and diagnostic images on a single surface. In alternative embodiments, however, the controller 256 may include both a non-interactive display and separate controls such as physical buttons and/or a joystick.

Although illustrative embodiments have been shown and described, a wide range of modification, change, and substitution is contemplated in the foregoing disclosure and in some instances, some features of the present disclosure may be employed without a corresponding use of the other features. For example, in some embodiments, the multi-modality processing systems 101 and 252 may be used to process non-cardiovascular diagnostic data such as data from cranial or peripheral arteries, as well as data from non-vascular body portions. Further, the systems 101 and 252 may be used to collect and process MRI or CT data, or may be utilized in computer assisted surgery (CAS) applications. Further, the modules described above in association with the multi-modality processing systems may be implemented in hardware, software, or a combination of both. And the processing systems may be designed to work on any specific architecture. For example, the systems may be executed on a single computer, local area networks, client-server networks, wide area networks, internets, hand-held and other portable and wireless devices and networks.

FIGS. 1-4 discussed above offer an example medical context in which a virtual pullback of an intravascular imaging device may be performed according to the various aspects of the present disclosure. In more detail, FIGS. 5-8 are screenshots of a user interface 300 for performing such virtual pullback of an intravascular imaging device. In certain embodiments, the user interface 300 may be implemented on the bedside control surface 118 (FIG. 2), the control room control surface 120 (FIG. 2), or the controller 256 (FIGS. 3-4). A human user/operator, for example a physician, may interactively engage with the user interface 300 to perform the virtual pullback of an intravascular imaging device, as discussed below in more detail.

Figure 5:
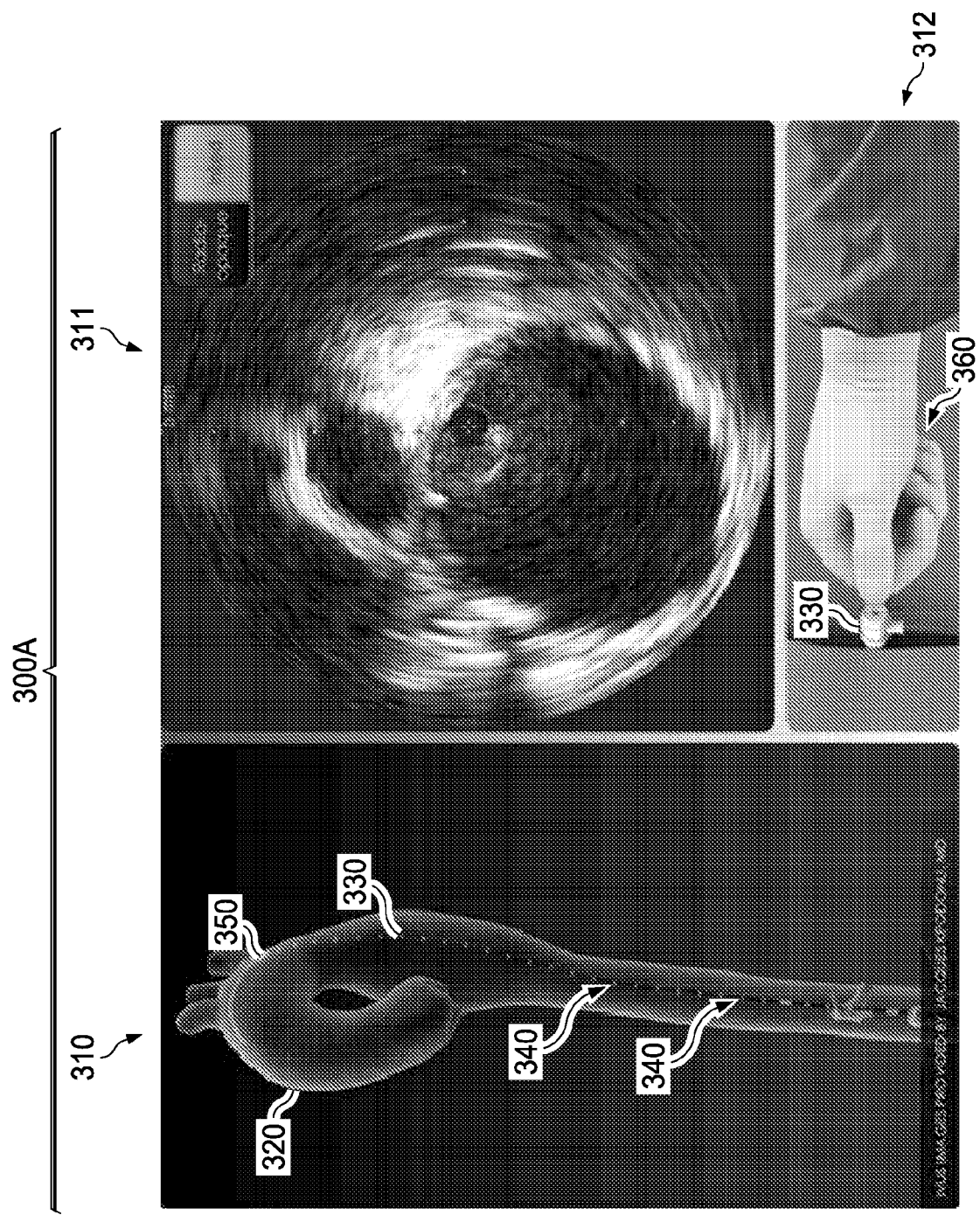
FIGS. 5-8 are user interfaces for performing a virtual pullback of an intravascular imaging device according to various aspects of the present disclosure.

The user interface 300A shown in FIG. 5 contains a plurality of views 310, 311, and 312. Each view 310-312 is shown in a respective virtual window of the user interface 300A. The views 310-312 collectively offer a virtual illustration of what is happening in a part of a human anatomy, with different types of imaging, in response to an operator's actions. The imaging content of the view 310 is different than the imaging content of the view 311. As such, it may be said that the views 310-311 are configured to display different imaging modalities. The simultaneous display of multiple imaging modalities in different views is referred to as co-registration, a more detailed discussion of which can be found in U.S. Pat. No. 7,930,014, titled "VASCULAR IMAGE CO-REGISTRATION" to Huennekens et al, and U.S. Pat. No. 8,298,147, titled "THREE-DIMENSIONAL CO-REGISTRATION FOR INTRAVASCULAR DIAGNOSIS AND THERAPY" to Huennekens et al, the entire disclosures of which are herein incorporated by reference in their entirety.

The view 310 includes a virtual representation of an anatomical region 320 of a human body. In the embodiment shown in FIG. 5, the anatomical region 320 is a blood vessel. However, the anatomical region 320 may include other parts of the human anatomy, such as different parts of the vasculature or any portion of the circulatory system. In some embodiments, the virtual representation of the anatomical region 320 is generated from a computer model, such as a two-dimensional or three-dimensional model of a typical human body. Such computer models may be manipulated by the user/operator in various ways, including moving, scaling, resizing, rotating, etc. In other embodiments, the virtual representation of the anatomical region 320 may be generated by actual imaging data, for example an angiogram, x-ray, MRI, CT, or other suitable imaging data taken from an actual patient (e.g., the patient 106 in FIGS. 2-3).

The view 310 also includes a virtual representation of an intravascular imaging device 330. In the embodiment shown in FIG. 5, the intravascular imaging device 330 is an IVUS catheter, for example the catheter 52 of FIG. 1. The virtual representation of the intravascular imaging device 330 is a substantially accurate representation of the actual intravascular imaging device 330. For example, the virtual representation accurately depicts the shape and geometry of the intravascular imaging device 330. The virtual representation of the intravascular imaging device 330 also includes a plurality of markers 340, illustrated as dots on the intravascular imaging device 330. These markers 340 denote units of length. For example, the distance between adjacent markers 340 may represent one centimeter (or another suitable unit of length). In this manner, the user/operator may gauge the dimensions of the anatomical region 320 relative to the intravascular imaging device 330. It is understood, however, that the markers 340 are not necessarily required, and they may or may not be implemented in alternative embodiments.

The virtual representation of the intravascular imaging device 330 also includes a virtual representation of an ultrasound transducer 350. Again, the virtual representation of the ultrasound transducer 350 may accurately depict the shape and geometry of the actual ultrasound transducer 350. The ultrasound transducer 350 is configured to capture cross-sectional ultrasound images of the anatomical region 320. In more detail, as the intravascular imaging device 330 is being moved with respect to the anatomical region 320 (for example being pulled out), the ultrasound transducer 350 continuously takes cross-sectional images of the anatomical region 320. Each cross-sectional ultrasound image corresponds to a particular location of the ultrasound transducer 350 inside the anatomical region 320. These ultrasound images are stored in a suitable computer data system, for example in the multi-modality processing system 101 of FIG. 2.

According to the various aspects of the present disclosure, the cross-sectional images are displayed in the view 311. Each displayed ultrasound image in the view 311 corresponds to the particular location of the virtual representation of the ultrasound transducer 350. The view 311 updates the displayed ultrasound images as the intravascular imaging device 330 is being virtually pulled back.

In the embodiment shown in FIG. 5, the view 312 is being used to facilitate the virtual pullback of the intravascular imaging device 330. In more detail, the view 312 shows another virtual representation of the intravascular imaging device 330, which also contains markers 340 (not shown in FIG. 5 but shown in FIG. 6) that denote units of length. Though the displayed sizes between the virtual representations of the intravascular imaging device 330 may vary between the two views 310 and 312, it is understood that they represent the same underlying actual device. Thus, as the virtual representation of the intravascular imaging device 330 is being pulled out of the patient body in the view 312, the virtual representation of the intravascular imaging device 330 is also pulled back in the same manner in the view 310. The amount of the pullback is the same in both views 310 and 312. For example, if the virtual representation of the intravascular imaging device 330 is pulled by three markers in the view 312, then the virtual representation of the intravascular imaging device 330 is also pulled by three markers in the view 310.

In the embodiment shown in FIG. 5, the view 312 utilizes a virtual hand 360 to perform the virtual pullback of the intravascular imaging device 330. Of course, other suitable virtual mechanisms may also be utilized in some embodiments to accomplish the virtual pullback of the intravascular imaging device 330.

Figure 6:
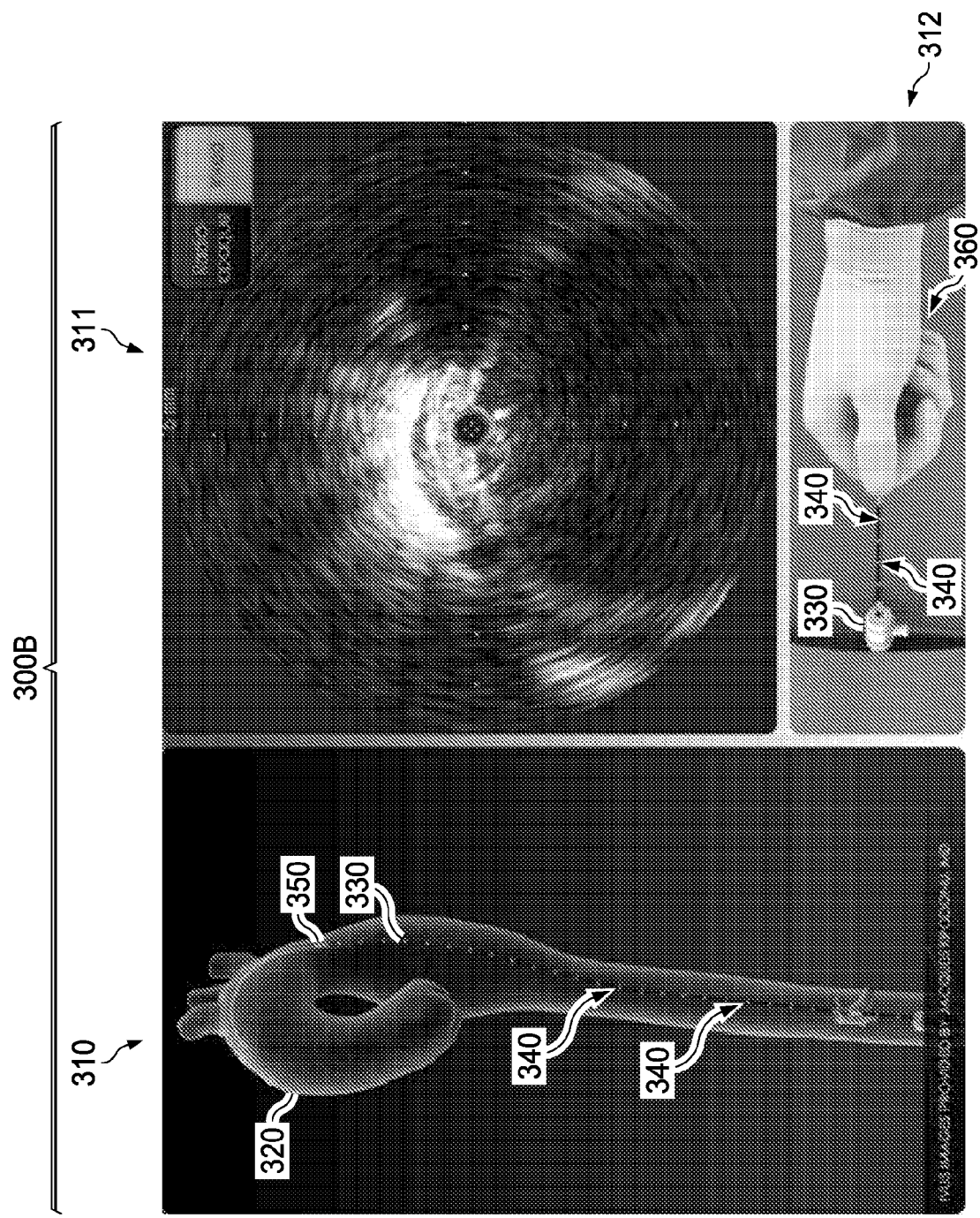

Referring now to FIG. 6, to provide a visual example of the discussions above, the user interface 300B illustrates another snapshot of the three different views 310-312. The user/operator may utilize the virtual hand 360 to pull back the virtual representation of the intravascular imaging device 330 in the view 312. For example, in embodiments where the user interface 300B is implemented on a touch-sensitive screen, the user/operator may user his/her finger(s) to touch and drag the virtual hand 360 to the right direction so as to pull on the virtual representation of the intravascular imaging device 330. In other embodiments where the user interface 300B is implemented on a non-touch-sensitive display, then a mouse or some other type of user input/output mechanism may be used to engage the virtual hand 360 to pull on the virtual representation of the intravascular imaging device 330.

As the virtual representation of the intravascular imaging device 330 is pulled in the view 312, it is also pulled in the view 310 in a substantially simultaneous manner (e.g., a delay of a number of milliseconds may be acceptable, particularly if such delay is not perceived by the user/operator). The user/operator may see in a clear visual manner where the intravascular imaging device 330 is relative to the anatomical region 320 throughout the virtual pullback process. Meanwhile, the ultrasound image in the view 311 is also continuously updated as the intravascular imaging device 330 is being virtually pulled. Again, each displayed ultrasound image in the view 311 corresponds to a location of the ultrasound transducer 350 inside the anatomical region 320.

Based on the above discussions, it can be seen that the interactive user interface 300 can be used as a powerful diagnostic tool. In some embodiments, an accurate virtual model is built for an intravascular organ (e.g., a particular blood vessel) of interest for a particular patient. In other words, this virtual model is customized for that specific patient. Such virtual model may be generated based on an angiogram, for example. In other embodiments, a more generic virtual model may be established, which may not be customized for any single patient. In any case, such virtual model is represented by the anatomical region 320 shown in the view 310 of the user interface 300. An actual intravascular imaging device (such as a catheter) is inserted into the intravascular organ of the target patient, and an actual pullback process of the intravascular imaging device is performed. As the actual pullback process takes place, ultrasound images at different locations of the intravascular organ are taken and recorded.

At a later time, the user/operator (which may be a physician or diagnostician) may perform the virtual pullback process of the intravascular imaging device 330 as discussed above, for example engaging the virtual hand 360 to pull on the intravascular imaging device 330. The virtual pullback process in a way simulates the actual pullback of the intravascular imaging device 330. During the virtual pullback, the user/operator may spot problem areas in one or more ultrasound images displayed in the view 311. When this occurs, the user/operator may refer to the view 310 and see the exactly location(s) in the anatomical region 320 that corresponds to the problematic ultrasound image(s). The availability of such locational information may allow the user/operator to perform better diagnoses or perform better medical procedures.

Figure 7:
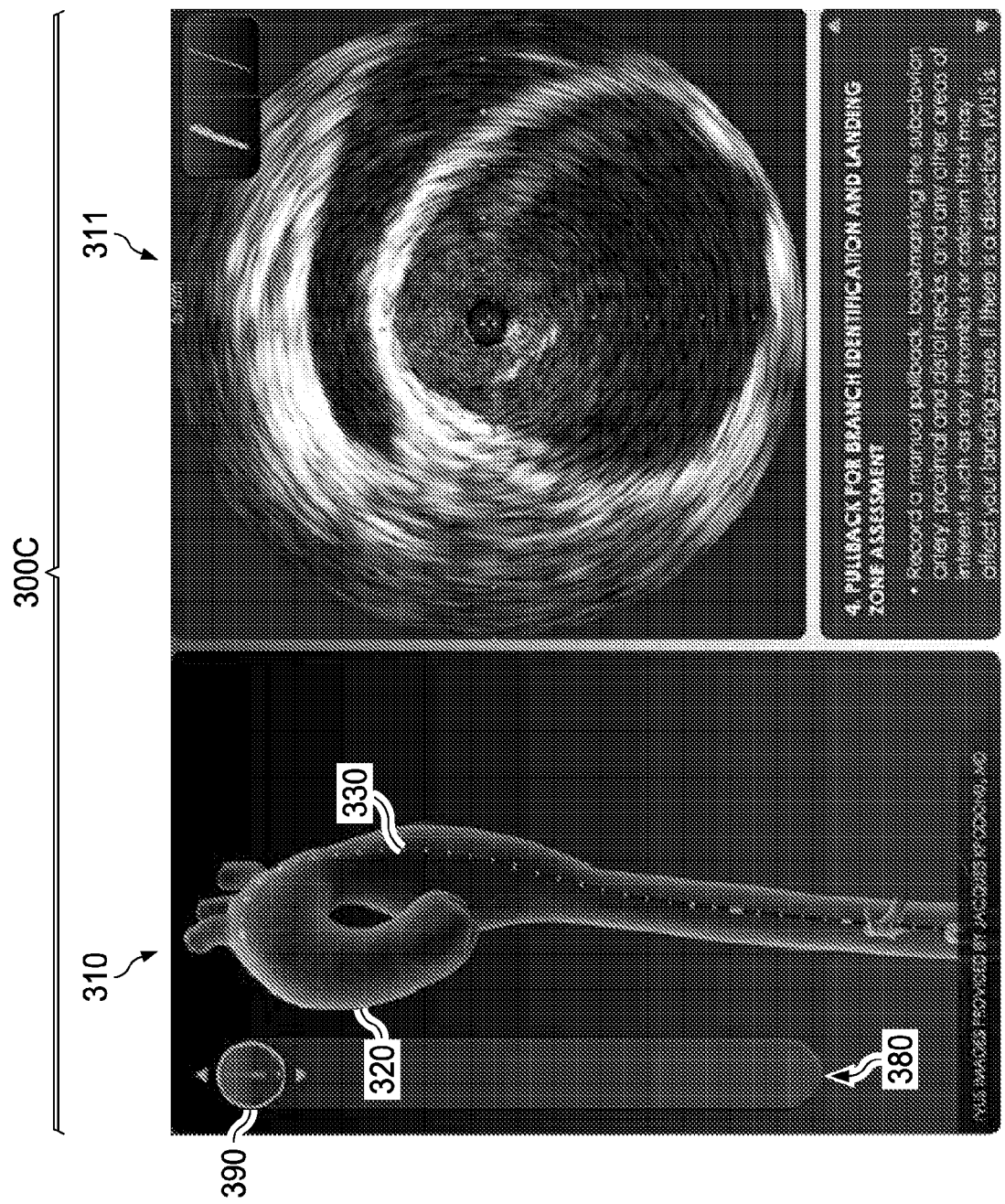
Figure 8:
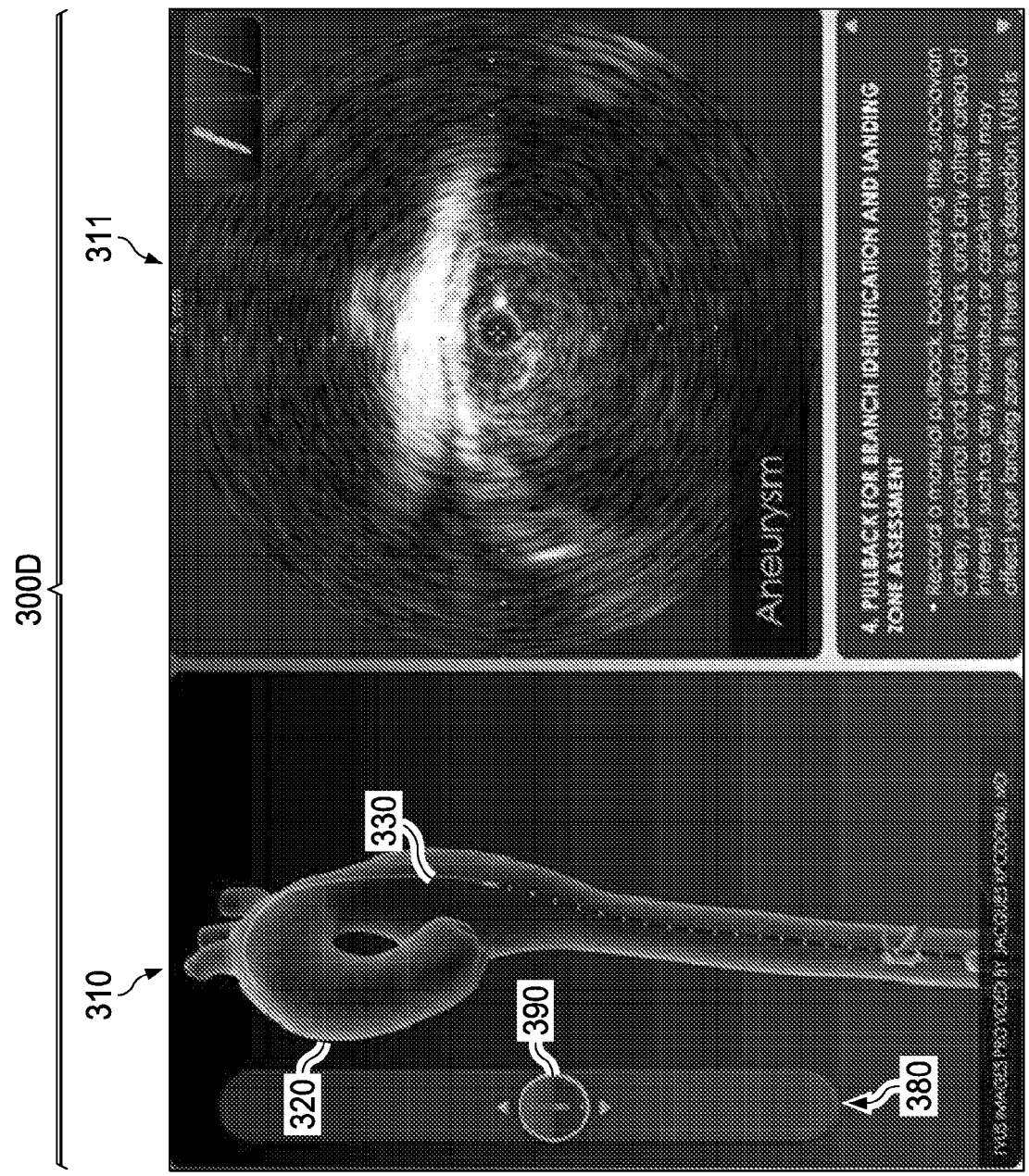

As discussed above, the virtual hand 360 is not the only available mechanism for performing the virtual pullback process. Referring now to FIGS. 7-8, another embodiment of the user interface to perform the virtual pullback is illustrated. In FIG. 7, the user interface 300C still includes the views 310 and 311, but does not need the view 312 that contains the virtual hand. Instead, the user interface 300C utilizes a virtual control mechanism 380 in the view 310 to facilitate the virtual pullback process.

In the embodiment shown in FIG. 7, the virtual control mechanism 380 is a slider, where an indicator 390 inside the slider 380 can be moved up or down by a touch-sensitive engagement or by a mouse or another suitable input/output device. The total length of the slider 380 may correspond to the total length of the intravascular imaging device 330. As the indicator 390 is moved up or down in the slider 380, the virtual representation of the intravascular imaging device 330 is also moved up or down inside the anatomical region 320. Therefore, the slider 380 and the indicator 390 may be used to accomplish the same task as the virtual hand 360 in FIGS. 5-6, which is to induce the virtual pullback of the intravascular imaging device 330.

For example, in FIG. 8, the indicator 390 is moved downwards in the slider 380. Correspondingly, the virtual representation of the intravascular imaging device 330 is also pulled downwards. Meanwhile, the ultrasound image displayed in the view 311 is updated to reflect the new position of the intravascular imaging device 330 inside the anatomical region 320. Again, the continuously updated display of the ultrasound image in the view 311 to reflect the positional movement of the intravascular imaging device 330. It is understood that other suitable virtual control mechanisms may be implemented in alternative embodiments to facilitate the virtual pullback process discussed above, but they are not discussed herein for reasons of simplicity.

The embodiments discussed above involve using the virtual pullback process for the diagnosis and/or performing medical procedures for an actual patient. However, this is not the only use of the virtual pullback process. In some embodiments, the virtual pullback process may also be used for mainly educational purposes. For example, in some embodiments, the user interface 300 (or something similar that allows for a demonstration of the virtual pullback process) may be implemented on an electronic tablet computer, such as an iPad, an iPhone, or other smart phones or tablets. The virtual representations of the anatomical region 320 or the intravascular imaging device 330 may not necessarily be tied to an actual patient or an actual product, but may simply be models for demonstration purposes. Nevertheless, the performance of the virtual pullback process as discussed above will still allow the user/operator to simulate the experience of a virtual pullback in the real world medical environment. That is, the ultrasound images are still continuously updated to reflect the movement of the intravascular imaging device.

In yet other embodiments, the virtual pullback process discussed above may be implemented in a more game-like environment. For example, a medical simulation game may be created that utilizes the user interface 300 discussed above. An example objective of the game may be to find a diseased area of a patient (e.g., by observing the ultrasound images and the corresponding virtual representation of the anatomical region). Another example objective of the game may be to perform one or more measurements in the anatomical region, which may involve using the virtual markers discussed above. To further enhance the gaming aspect of the virtual pullback process and to make the games more challenging, these game objectives may also need to be completed within a predetermined amount of time.

It is also understood that the virtual pullback process discussed above may be implemented on any suitable electronic device, for example an electronic tablet such as the iPad or an Android-powered tablet, smartphones such as iPhones, Android-powered smartphones, windows phones, blackberries, laptop or desktop computers, or suitable medical devices and/or systems from a medical device manufacturer (e.g., the s5 imaging system from Volcano, Corp.). To the extent applicable, the touch screens of these electronic devices may be used as the touch-sensitive control mechanism on which an operator can perform the virtual pullback process. Alternatively, other input/output means such as mouses or keyboards may also be used to perform the virtual pullback process.

The virtual pullback process may also be used in medical contexts where a physician may be remotely located. For example, some robotics-assisted medical systems allow a physician to be situated remotely from a patient but still able to place or pullback a catheter (or other intravenous medical devices) in a target patient. In these scenarios, the remotely-located physician may be able to perform a virtual medical procedure similar to the virtual pullback process discussed above on an interactive device (e.g., a touch screen), and the robotics of the medical system may perform the actual medical procedure based on the input received on the interactive device according to the physician's actions. In other words, the robotics involved may simulate the physician's actions performed in a virtual context.

It is also understood that the user interface 300 discussed above may be configured to optionally display various interactions with a given therapy. For example, the user interface may be configured to show the stent or treatment device position before or after its deployment. Other suitable interactions are envisioned but are not discussed herein for reasons of simplicity.

Figure 9:
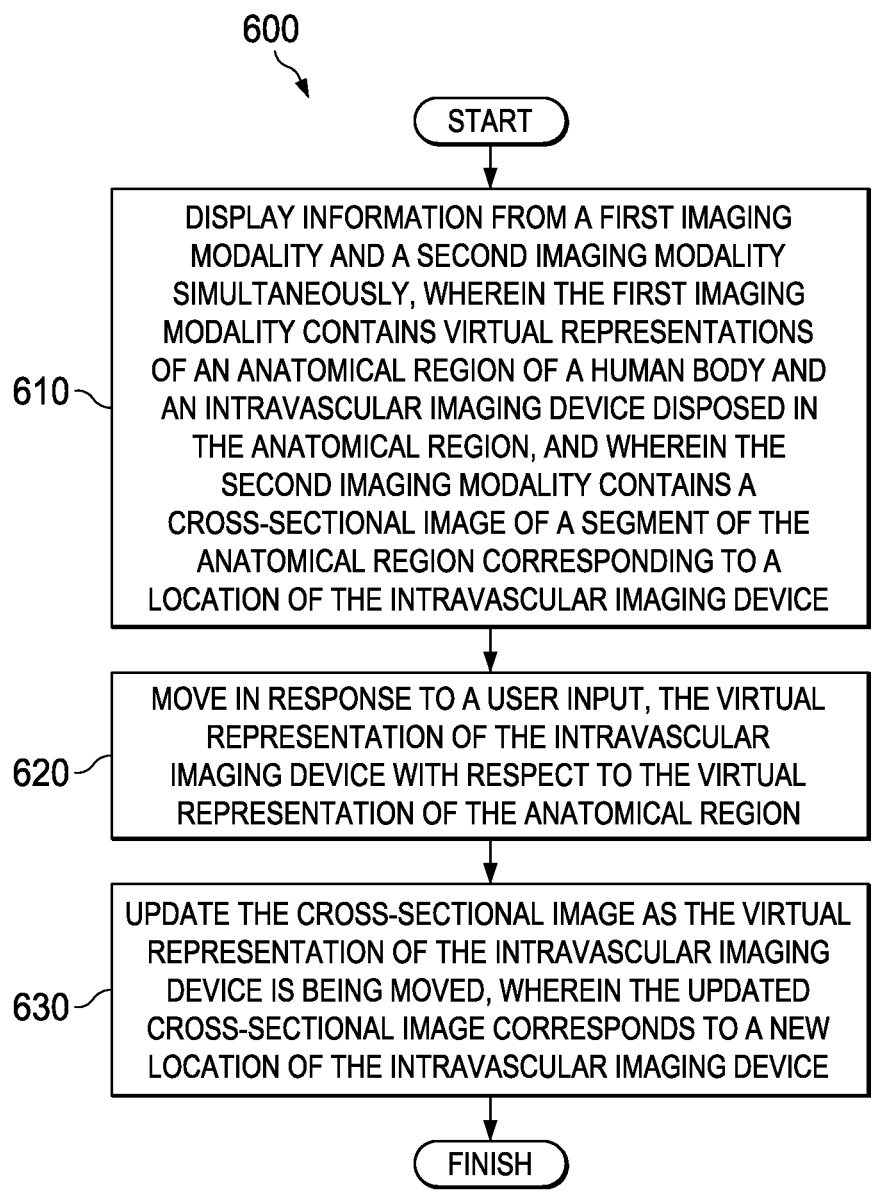
FIG. 9 is a flowchart illustrating a method for performing a virtual pullback of an intravascular imaging device according to various aspects of the present disclosure.

FIG. 9 is a flowchart of a method 600 for simulating an intravascular procedure in a virtual environment according to various aspects of the present disclosure. The method 600 includes a step 610, in which information is displayed from a first view and a second view simultaneously. The first view contains virtual representations of an anatomical region of a human body and an intravascular imaging device disposed in the anatomical region. The second view contains a cross-sectional image of a segment of the anatomical region corresponding to a location of the intravascular imaging device.

The method 600 includes a step 620, in which the virtual representation of the intravascular imaging device is moved with respect to the virtual representation of the anatomical region. The step 620 is performed in response to a user input.

The method 600 includes a step 630, in which the cross-sectional image is updated as the virtual representation of the intravascular imaging device is being moved. The updated cross-sectional image corresponds to a new location of the intravascular imaging device.

It is understood that additional steps may be performed to complete the simulation of an intravascular procedure in a virtual environment. However, these additional steps are not discussed herein for reasons of simplicity.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of displaying an intravascular procedure in a virtual environment, the method comprising:

displaying information from a first view, a second view, and a third view simultaneously, wherein the first view contains a virtual representation of an anatomical region of a human body and a first virtual representation of an intravascular imaging device disposed in the anatomical region, wherein the second view contains a cross-sectional image of a segment of the anatomical region corresponding to a location of the intravascular imaging device, and wherein the third view contains a second virtual representation of the intravascular imaging device and a virtual control mechanism for moving the second virtual representation of the intravascular imaging device, and wherein the first and second virtual representations of the intravascular imaging device each include a body and a plurality of markers disposed on the body, and wherein the first and second virtual representations of the intravascular imaging device each include a shape and a geometry of the intravascular imaging device;

moving the second virtual representation of the intravascular imaging device in response to the virtual control mechanism being moved by a user, wherein the first virtual representation of the intravascular imaging device is moved with respect to the virtual representation of the anatomical region to correspond with the moving of the second virtual representation of the intravascular imaging device; and updating the cross-sectional image as the first virtual representation and the second virtual representation of the intravascular imaging device are being moved, wherein the updated cross-sectional image corresponds to a new location of the intravascular imaging device resulting from the second virtual representation of the intravascular imaging device being moved by the user via the virtual control mechanism.

2. The method of claim 1, wherein the anatomical region comprises a part of a circulatory system.

3. The method of claim 1, wherein the virtual representation of the anatomical region comprises a three-dimensional computer model of the anatomical region.

4. The method of claim 1, wherein the virtual representation of the anatomical region comprises an angiogram of the anatomical region of an actual patient.

5. The method of claim 1, wherein the cross-sectional image comprises an ultrasound image.

6. The method of claim 1, wherein the intravascular imaging device comprises a catheter with a transducer implemented thereon.

7. The method of claim 1, wherein the virtual control mechanism comprises a virtual representation of a human hand.

8. The method of claim 1, wherein the first view further comprises a further virtual control mechanism for moving the first virtual representation of the intravascular imaging device in response to a user input.

9. The method of claim 1, wherein the displaying is performed using a touch-sensitive screen, and wherein the virtual control mechanism being moved by the user is detected through the touch-sensitive screen.

10. The method of claim 1, wherein the first view and the second view are configured to display different imaging modalities.

11. The method of claim 1, wherein the first virtual representation of the intravascular imaging device further includes an ultrasound transducer.

12. A method of performing a virtual medical operation, comprising:
- displaying, on an electronic screen, a first view, a second view, and a third view simultaneously, wherein the first view contains a virtual representation of an anatomical region of a human body and a first virtual representation of an intravascular imaging device disposed in the anatomical region, wherein the second view contains a cross-sectional image of a segment of the anatomical region corresponding to a location of the intravascular imaging device, and wherein the third view contains a second virtual representation of the intravascular imaging device outside the anatomical region, wherein the first and second virtual representations of the intravascular imaging device each include a body and a plurality of markers disposed on the body, wherein the first and second virtual representations of the intravascular imaging device each include a shape and a geometry of the intravascular imaging device;
- pulling, in response to a user input, the second virtual representation of the intravascular imaging device in the third view;
- moving, in the first view, the first virtual representation of the intravascular imaging device with respect to the virtual representation of the anatomical region as the second virtual representation of the intravascular imaging device is being pulled; and
- updating, in the second view, the cross-sectional image in a manner to track a movement of the intravascular imaging device in the first view.

13. The method of claim 12, wherein:
- the anatomical region includes a part of a circulatory system;
- the virtual representation of the anatomical region includes an angiogram of the anatomical region or a three-dimensional model of the anatomical region;
- the cross-sectional image includes an ultrasound image;
- the intravascular imaging device includes a catheter having a transducer implemented thereon; and
- the electronic screen includes a touch-sensitive screen.

14. The method of claim 12, wherein the first virtual representation of the intravascular imaging device further includes an ultrasound transducer.

15. An electronic apparatus configured to perform a virtual pullback of an intravascular imaging device, the electronic apparatus comprising:
- a screen configured to display an output to a user;
- a memory storage component configured to store programming code; and
- a computer processor configured to execute the programming code to perform the following tasks:
  - displaying, on the screen, information from a first view, a second view, and a third view simultaneously, wherein the first view contains a virtual representation of an anatomical region of a human body and a first virtual representation of an intravascular imaging device disposed in the anatomical region, wherein the second view contains a cross-sectional image of a segment of the anatomical region corresponding to a location of the intravascular imaging device, and wherein the third view contains a second virtual representation of the intravascular imaging device and a virtual control mechanism for moving the second virtual representation of the intravascular imaging device, and wherein the first and second virtual representations of the intravascular imaging device each include a body and a plurality of markers disposed on the body, and wherein the first and second virtual representations of the intravascular imaging device each include a shape and a geometry of the intravascular imaging device;
  - moving the second virtual representation of the intravascular imaging device in response to the virtual control mechanism being moved by a user, wherein the first virtual representation of the intravascular imaging device is moved with respect to the virtual representation of the anatomical region to correspond with the moving of the second virtual representation of the intravascular imaging device; and
  - updating the cross-sectional image as the first virtual representation and the second virtual representation of the intravascular imaging device are being moved, wherein the updated cross-sectional image corresponds to a new location of the intravascular imaging device resulting from the second virtual representation of the intravascular imaging device being moved by the user via the virtual control mechanism.

16. The electronic apparatus of claim 15, wherein the anatomical region comprises a part of a circulatory system.

17. The electronic apparatus of claim 15, wherein the virtual representation of the anatomical region comprises a three-dimensional computer model of the anatomical region or an angiogram of the anatomical region of an actual patient.

18. The electronic apparatus of claim 15, wherein the cross-sectional image comprises an ultrasound image.

19. The electronic apparatus of claim 15, wherein the intravascular imaging device comprises a catheter with a transducer implemented thereon.

20. The electronic apparatus of claim 15, wherein the virtual control mechanism comprises a virtual representation of a human hand.

21. The electronic apparatus of claim 15, wherein the first view further comprises a virtual control mechanism for moving the virtual representation of the intravascular imaging device in response to the user input.

22. The electronic apparatus of claim 15, wherein the screen is a touch-sensitive screen, and wherein the virtual control mechanism being moved by the user is detected through the touch-sensitive screen.

23. The electronic apparatus of claim 15, wherein the first virtual representation of the intravascular imaging device further includes an ultrasound transducer.

24. An apparatus comprising a non-transitory, tangible machine-readable storage medium storing a computer program, wherein the computer program contains machine-readable instructions that when executed electronically by computer processors, perform:
- displaying, on a touch-sensitive screen, information from a first view, a second view, and a third view simultaneously, wherein the first view contains a virtual representation of an anatomical region of a human body and a first virtual representation of an intravascular imaging device disposed in the anatomical region, wherein the second view contains a cross-sectional image of a segment of the anatomical region corresponding to a location of the intravascular imaging device, and wherein the third view contains a second virtual representation of the intravascular imaging device and a virtual control mechanism for moving the second virtual representation of the intravascular imaging device, and wherein the first and second virtual representations of the intravascular imaging device each include a body and a plurality of markers disposed on the body, and wherein the first and second virtual representations of the intravascular imaging device each include a shape and a geometry of the intravascular imaging device;

moving the second virtual representation of the intravascular imaging device in response to the virtual control mechanism being pulled by a user, wherein the first virtual representation of the intravascular imaging device is moved with respect to the virtual representation of the anatomical region to correspond with the moving of the second virtual representation of the intravascular imaging device; and updating the cross-sectional image as the first virtual representation and the second virtual representation of the intravascular imaging device are being moved, wherein the updated cross-sectional image corresponds to a new location of the intravascular imaging device resulting from the second virtual representation of the intravascular imaging device being moved by the user via the virtual control mechanism.

25. The apparatus of claim 24, wherein:

the anatomical region comprises a part of a circulatory system;

the virtual representation of the anatomical region comprises a three-dimensional computer model of the anatomical region or an angiogram of the anatomical region of an actual patient;

the cross-sectional image comprises an ultrasound image; and the intravascular imaging device comprises a catheter with a transducer implemented thereon.

26. The apparatus of claim 24, wherein:

the virtual control mechanism comprises a virtual representation of a human hand.

27. The apparatus of claim 24, wherein the first view further comprises a virtual control mechanism for moving the virtual representation of the intravascular imaging device in response to the user input.

28. The apparatus of claim 24, wherein the first virtual representation of the intravascular imaging device further includes an ultrasound transducer.

\* \* \* \* \*